US009107774B2

(12) United States Patent
Nakamura et al.

(10) Patent No.: US 9,107,774 B2
(45) Date of Patent: Aug. 18, 2015

(54) MANUFACTURING METHOD AND MANUFACTURING EQUIPMENT OF COMPOSITE SHEET OF ABSORBENT ARTICLE

(75) Inventors: Taishi Nakamura, Kagawa (JP); Shinichi Ishikawa, Kagawa (JP); Jun Okuda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 872 days.

(21) Appl. No.: 13/262,659

(22) PCT Filed: Mar. 29, 2010

(86) PCT No.: PCT/JP2010/055541
§ 371 (c)(1),
(2), (4) Date: Dec. 9, 2011

(87) PCT Pub. No.: WO2010/113856
PCT Pub. Date: Oct. 7, 2010

(65) Prior Publication Data
US 2012/0077660 A1 Mar. 29, 2012

(30) Foreign Application Priority Data
Apr. 3, 2009 (JP) .................................. 2009-091504

(51) Int. Cl.
B31B 49/00 (2006.01)
A61F 13/15 (2006.01)
B65H 37/04 (2006.01)

(52) U.S. Cl.
CPC .......... *A61F 13/15609* (2013.01); *B65H 37/04* (2013.01); *A61F 13/15593* (2013.01); *B65H 2801/57* (2013.01)

(58) Field of Classification Search
CPC ........ B31B 49/00; B32B 37/02; B32B 38/00; B32B 38/18; D04H 17/00; A61F 13/15593; A61F 13/15609
USPC ......... 493/374, 380–382; 156/73.6, 161, 163, 156/323, 461; 28/116
See application file for complete search history.

(56) References Cited

U.S. PATENT DOCUMENTS 5,147,487 A * 9/1992 Nomura et al. ................ 156/164
5,525,175 A * 6/1996 Blenke et al. ................. 156/161
(Continued)

FOREIGN PATENT DOCUMENTS

EP 2338450 A1 6/2011
JP 11322147 A 11/1999
(Continued)

OTHER PUBLICATIONS

Extended European Search Report issued May 19, 2014, corresponds to European patent application No. 10758627.3.
(Continued)

*Primary Examiner* — Thanh Truong
*Assistant Examiner* — Justin Citrin
(74) *Attorney, Agent, or Firm* — Lowe Hauptman & Ham, LLP

(57) ABSTRACT

A manufacturing method of a composite sheet of an absorbent article, the method includes joining a continuous body of an elastic member in a predetermined meander pattern in respect to a continuous body of a sheet transported continuously in a transporting direction, the method includes: transporting the continuous body of the sheet by wrapping the continuous body of the sheet around an outer circumferential face of a transporting roll that rotates in a direction along the transporting direction; and joining the continuous body of the elastic member to a portion of the continuous body of the sheet wrapped around the transporting roll by feeding the continuous body of the elastic member to the continuous body of the sheet via an oscillating arm that oscillates in an intersecting direction intersecting the transporting direction with a spindle portion as a swivel fulcrum, wherein the oscillating arm includes an oscillating end side roller arranged at an oscillating end side of the oscillating arm and a spindle portion side roller arranged at a spindle portion side, wherein in the joining, the continuous body of the elastic member supplied toward the spindle portion side roller through a supply route along a rotational central axis direction of the spindle portion is put around an outer circumferential face of the spindle portion side roller and an outer circumferential face of the oscillating end side roller successively and guided to the continuous body of the sheet, and a driving force to make the oscillating arm oscillate is input at a position on the oscillating arm different from the spindle portion.

7 Claims, 7 Drawing Sheets

(56) References Cited

U.S. PATENT DOCUMENTS

| | | | |
|---|---|---|---|
| 5,766,411 A * | 6/1998 | Wilson | 156/495 |
| 6,287,409 B1 | 9/2001 | Stephany | |
| 6,589,149 B1 | 7/2003 | VanEperen et al. | |
| 2002/0023706 A1 | 2/2002 | Vogt et al. | |
| 2006/0185135 A1 | 8/2006 | Yamamoto et al. | |

FOREIGN PATENT DOCUMENTS

| | | | |
|---|---|---|---|
| JP | 2003517880 A | 6/2003 | |
| JP | 2004505725 A | 2/2004 | |
| JP | 2004159866 A | 6/2004 | |
| JP | 2008230734 A | 10/2008 | |

OTHER PUBLICATIONS

Office Action issued Oct. 14, 2013, corresponds to Eurasian patent application No. 201101447.

Office Action dated Dec. 10, 2013, corresponds to Chinese patent application No. 201080014906.9.

International Search Report for PCT/JP2010/055541 dated Jun. 15, 2010.

Office Action issued Apr. 15, 2013 corresponds to Chinese patent application No. 201080014906.9.

Office Action issued Feb. 13, 2015, corresponding to Taiwanese patent application No. 099110356.

Office Action dated Apr. 24, 2015, corresponding to Vietnamese patent application No. 1-2011-02345.

* cited by examiner

B-B CROSS SECTION

B-B CROSS SECTION

MANUFACTURING METHOD AND MANUFACTURING EQUIPMENT OF COMPOSITE SHEET OF ABSORBENT ARTICLE

RELATED APPLICATIONS

The present application is a national phase of PCT/JP2010/055541, filed Mar. 29, 2010 and is based on, and claims priority from, Japanese Application Number 2009-091504, filed Apr. 3, 2009.

TECHNICAL FIELD

The present invention relates to manufacturing methods and manufacturing equipment of composite sheets of absorbent articles.

BACKGROUND ART

A disposable diaper and the like have conventionally been known as an example of an absorbent article that absorbs body waste fluid. In its manufacturing line, a continuous body of a sheet that is transported continuously in a transporting direction is attached continuously with a continuous body of an elastic member in a meander pattern such as a sine curve.

As an example of such an attaching method, Patent Literature 1 discloses that a continuous body of the elastic member 211 is attached to a sheet 213 using an oscillating arm 203 that swivels and oscillates around a rotational central axis C201 of a predetermined spindle portion 201 as shown in a side view of FIG. 1A, and a B-B cross sectional view of FIG. 1A as shown in FIG. 1B. That is, a through hole is provided at an oscillating end 203a of the oscillating arm 203, and a continuous body of the elastic member 211 is passed through this through hole. With the oscillating movement of the oscillating arm 203 around the rotational central axis C201, the oscillating end 203a is oscillated in a CD direction that intersects the transporting direction of the sheet 213, thereby a continuous body of the elastic member 211 is attached in a predetermined meander pattern in respect to the sheet 213 that is transported in the transporting direction.

Further, PTL 1 also discloses a driving mechanism of the oscillating arm 203, that is, there is described that a drive rotational shaft of a motor 205 is directly connected concentrically to a spindle portion 201 of the oscillating arm 203.

CITATION LIST

Patent Literature

PTL 1: JP-A-2004-159866

SUMMARY OF INVENTION

Technical Problem

Here, a continuous body of the elastic member 211 is directly sent to the through hole of the oscillating end 203a of the oscillating arm 203 from a guide roller 207 supported by a portion other than the oscillating arm 203. Thus, in the case where an amplitude amount of oscillation of the oscillating arm 203 is large, there is fear that a travel state of the continuous body of the elastic member 211 becomes unstable, such as it becomes likely for the continuous body of the elastic member 211 to fall of the guide roller 207.

From the view of stability of this travel state, as in the side view of FIG. 2A, and the B-B cross sectional view in FIG. 2A shown in FIG. 2B, it is considered effective to support a guide roller 207a in a portion to the spindle portion 201 side in the oscillating arm 203, and at the time of supplying the continuous body of the elastic member 211 toward the guide roller 207a, to make a supply route P211 follow along a direction of a rotational central axis C201 of the spindle portion 201.

Further, at the upper side of the spindle portion 201, it is possible to set the above described preferable supply route P211 as shown in FIG. 2A. However, as shown in FIG. 2A in a chain double-dashed line, there is a case where the preferable supply route 211 has to be set at a lower side of the spindle portion 201.

But, in this case, the motor 205 is provided at the lower side of the spindle portion 201, so that the motor 205 gets in the way, and it becomes difficult to set the above preferable supply route P211.

The invention has been made in view of the problems described above, and an advantage is that it is possible to easily set a supply route of a continuous body of an elastic member that goes toward a spindle portion along a rotational central axis direction of the spindle portion of an oscillating arm, and thereby to improve travel stability of the continuous body of the elastic member.

Solution to Problem

In order to achieve the above-described advantages, an aspect of the invention is a manufacturing method of a composite sheet of an absorbent article, the method including joining a continuous body of an elastic member in a predetermined meander pattern in respect to a continuous body of a sheet transported continuously in a transporting direction, the method including:

transporting the continuous body of the sheet by wrapping the continuous body of the sheet around an outer circumferential face of a transporting roll that rotates in a direction along the transporting direction; and joining the continuous body of the elastic member to a portion of the continuous body of the sheet wrapped around the transporting roll by feeding the continuous body of the elastic member to the continuous body of the sheet via an oscillating arm that oscillates in an intersecting direction intersecting the transporting direction with a spindle portion as a swivel fulcrum, wherein the oscillating arm includes an oscillating end side roller arranged at an oscillating end side of the oscillating arm and a spindle portion side roller arranged at a spindle portion side, wherein in the joining, the continuous body of the elastic member supplied toward the spindle portion side roller through a supply route along a rotational central axis direction of the spindle portion is put around an outer circumferential face of the spindle portion side roller and an outer circumferential face of the oscillating end side roller successively and guided to the continuous body of the sheet, and wherein a driving force to make the oscillating arm oscillate is input at a position on the oscillating arm different from the spindle portion.

Another aspect of the invention is a manufacturing equipment of a composite sheet of an absorbent article, the equipment including joining a continuous body of an elastic member in a predetermined meander pattern in respect to a continuous body of a sheet transported continuously in a transporting direction, the equipment including:

a transporting roll that rotates in a direction along the transporting direction and transports the continuous body of the sheet by wrapping around the continuous body of the sheet on an outer circumferential face; and an oscillating arm that oscillates in an intersecting direction intersecting the transporting direction with a spindle portion as a swivel fulcrum and that joins the continuous body of the elastic member to a portion of the continuous body of the sheet wrapped around the transporting roll by feeding the continuous body of the elastic member to the continuous body of the sheet, wherein the oscillating arm includes an oscillating end side roller arranged at an oscillating end side of the oscillating arm and a spindle portion side roller arranged at a spindle portion side, wherein the continuous body of the elastic member supplied toward the spindle portion side roller through a supply route along a rotational central axis direction of the spindle portion is put around an outer circumferential face of the spindle portion side roller and an outer circumferential face of the oscillating end side roller successively and guided to the continuous body of the sheet, and wherein a driving force to make the oscillating arm oscillate is input at a position on the oscillating arm different from the spindle portion.

Other features of the present invention will be made clear through the present specification with reference to the accompanying drawings.

Advantageous Effects of Invention

According to this invention, it is possible to easily set a supply route of a continuous body of an elastic member that goes toward a spindle portion along a rotational central axis direction of the spindle portion of an oscillating arm, and thereby can improve travel stability of the continuous body of the elastic member.

DESCRIPTION OF EMBODIMENTS

Figure 1A:
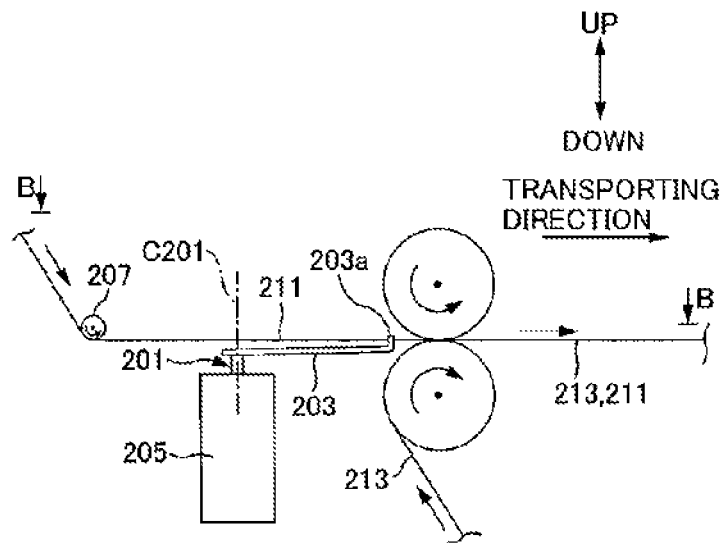
FIG. 1A is a perspective view of a conventional method of attaching a continuous body of an elastic member 211 in a predetermined meander pattern in respect to a continuous body of a sheet 213.
Figure 1B:
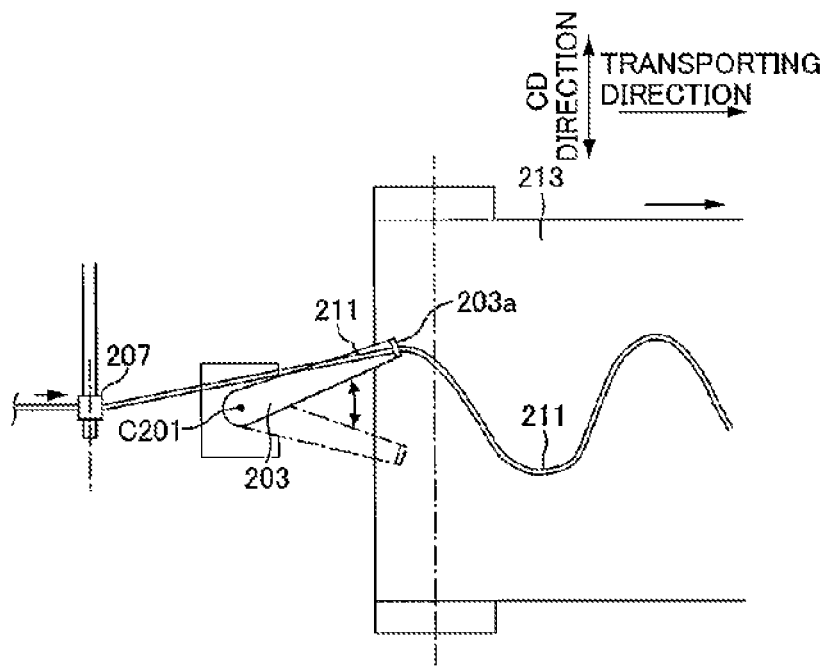
FIG. 1B is a cross-sectional view taken along B-B in FIG. 1A.
Figure 2A:
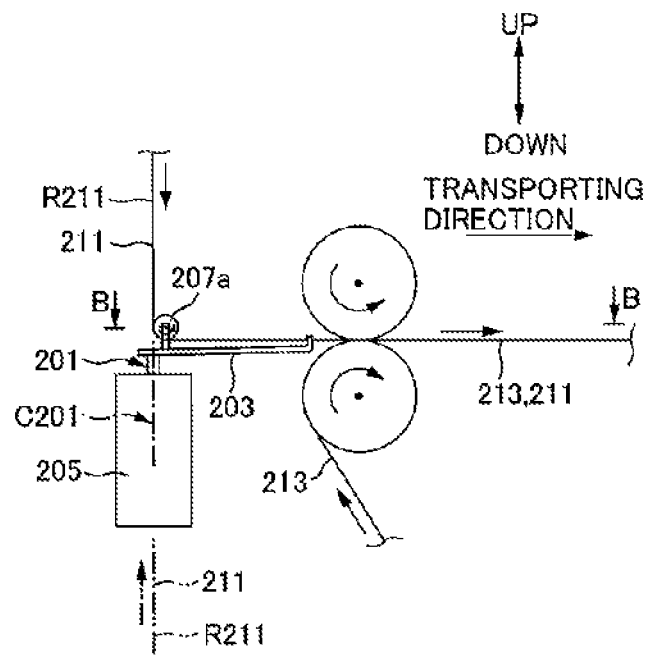
FIG. 2A is a perspective view of a method of the same illustrative example.
Figure 2B:
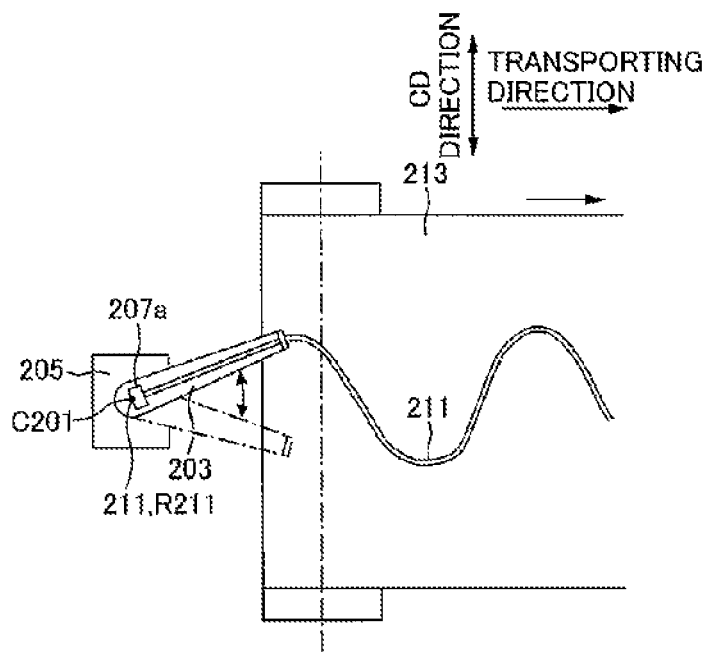
FIG. 2B is a cross-sectional view taken along B-B in FIG. 2A.

At least the following matters will become clear through the description of the present specification and the accompanying drawings.

A manufacturing method of a composite sheet of an absorbent article, the method including joining a continuous body of an elastic member in a predetermined meander pattern in respect to a continuous body of a sheet transported continuously in a transporting direction, the method including:

transporting the continuous body of the sheet by wrapping the continuous body of the sheet around an outer circumferential face of a transporting roll that rotates in a direction along the transporting direction; and joining the continuous body of the elastic member to a portion of the continuous body of the sheet wrapped around the transporting roll by feeding the continuous body of the elastic member to the continuous body of the sheet via an oscillating arm that oscillates in an intersecting direction intersecting the transporting direction with a spindle portion as a swivel fulcrum, wherein the oscillating arm includes an oscillating end side roller arranged at an oscillating end side of the oscillating arm and a spindle portion side roller arranged at a spindle portion side, wherein in the joining, the continuous body of the elastic member supplied toward the spindle portion side roller through a supply route along a rotational central axis direction of the spindle portion is put around an outer circumferential face of the spindle portion side roller and an outer circumferential face of the oscillating end side roller successively and guided to the continuous body of the sheet, and wherein a driving force to make the oscillating arm oscillate is input at a position on the oscillating arm different from the spindle portion.

With this manufacturing method of the composite sheet of the absorbent article, it is possible to oscillate the oscillating arm without directly connecting concentrically a drive rotational axis of the driving source of the oscillating arm in respect to the spindle portion. Thus, the driving source does not have to be arranged close to the spindle portion, and as a result the continuous body of the elastic member can be easily supplied toward the spindle portion through the supply route along the rotational central axis direction of the spindle portion.

Further, the portion at the spindle portion side of the oscillating arm is provided with the spindle portion side roller, and the continuous body of the elastic member is fed to the spindle portion side roller along the rotational central axis direction of the spindle portion. Thus, the movement in the intersecting direction of the continuous body of the elastic member that may occur due to the oscillating movement of the oscillating arm appears mainly as a torsion in the portion of the continuous body of the elastic member positioned at the upstream side than the spindle portion side roller and is absorbed there, and for this reason falling off of the continuous body of the elastic member from the spindle portion side roller is effectively prevented. As a result, stability in the travel state of the continuous body of the elastic member is obtained.

A manufacturing method of a composite sheet of an absorbent article, wherein preferably the oscillating end side roller and the spindle portion side roller are arranged on a face of the oscillating arm on a side opposing the transporting roll, the spindle portion is formed with a communicating space that communicates the side opposing the transporting roll and a side not opposing the transporting roll, along the rotational central axis direction of the spindle portion, the continuous body of the elastic member that is fed through the supply route along the rotational central axis direction of the spindle portion reaches a face of the oscillating arm on the side not opposing the transporting roll, and ends at the spindle portion side roller by passing through the communicating space.

With this manufacturing method of the composite sheet of the absorbent article, in the case where the continuous body of the elastic member is fed toward a face of the oscillating arm that is at a side opposite the face on which the spindle portion side roller is provided (namely, the surface on a side not opposing the transporting roll), it becomes possible to surely put the continuous body of the elastic member around the spindle portion side roller, by passing it through the communicating space of the spindle portion.

A manufacturing method of a composite sheet of an absorbent article, wherein preferably the communicating space is a through hole formed in the spindle portion along the rotational central axis direction of the spindle portion.

With this manufacturing method of the composite sheet of the absorbent article, in the case where the continuous body of the elastic member is fed toward a face of the oscillating arm that is at a side opposite the face on which the spindle portion side roller is provided (namely, the face on a side not opposing the transporting roll), it becomes possible to surely put the continuous body of the elastic member around the spindle portion side roller, by passing it through the communicating space of the spindle portion.

A manufacturing method of a composite sheet of an absorbent article, wherein preferably the rotational central axis of the spindle portion is in contact with an outer circumferential face of the spindle portion side roller.

With this manufacturing method of the composite sheet of the absorbent article, the rotational central axis of the spindle portion is contacting the outer circumferential face of the spindle portion side roller. Thus, the continuous body of the elastic member is surely fed to the spindle portion side roller along a rotational central axis direction of the spindle portion. As a result, a movement in the intersecting direction of the continuous body of the elastic member that may occur due to the oscillating movement of the oscillating arm surely appears as torsion in the portion of the elastic member that is to the upstream side than the spindle portion side roller and is absorbed there. As a result, falling off of the continuous body of the elastic member from the spindle portion side roller can be effectively prevented.

A manufacturing method of a composite sheet of an absorbent article, wherein preferably in order to input the driving force to the oscillating arm,
a driving source having a drive rotational axis that is rotatingly driven and
a conversion transmission mechanism that converts a rotating movement of the drive rotational axis to a reciprocating movement and transmits the reciprocating movement to the position on the oscillating arm
are included,
the conversion transmission mechanism having
a rotating member attached integrally to the drive rotational axis and
a coupling member that couples the position on the oscillating arm to a position eccentric from the drive rotational axis of the rotating member, and
the rotating member is set with a plurality of the eccentric positions each having different eccentric amounts from each other.

With this manufacturing method of the composite sheet of the absorbent article, by selecting the eccentric position on the rotating member, the amplitude amount of the oscillating arm can be changed. Thus, by selecting the eccentric position according to the meander pattern of the elastic member, it is possible to easily change to a desired meander pattern.

A manufacturing method of a composite sheet of an absorbent article, wherein preferably the transporting roll rotates around a rotational axis,
the oscillating end side roller and the spindle portion of the oscillating arm are arranged so as to sandwich the rotational axis of the transporting roll in between, and
a direction of travel of the continuous body of the elastic member is reversed by the oscillating end side roller and the continuous body of the elastic member is supplied to the transporting roll.

With this manufacturing method of the composite sheet of the absorbent article, it becomes possible to ensure a large wrap around angle of the continuous body of the elastic member to the oscillating end side roller. For this reason, the continuous body of the elastic member can be tightly held on the outer circumferential face of the oscillating end side roller. As a result, stability in the travel state of the continuous body of the elastic member, such as being able to effectively prevent falling off of the continuous body of the elastic member from the oscillating end side roller, is obtained.

Further, in the case where the continuous body of the elastic member is a continuous body of a strip member, the continuous body of the strip member can be fed to the sheet by being maintained in a substantially flat shape, and as a result, the continuous body of the strip member can be made to come in surface contact with the sheet and can be joined. Namely, by reversing the above-described travel direction, the continuous body of the strip members is wrapped around the outer circumferential face of the oscillating end side roller at a large wrap around angle. Therefore, the continuous body of the strip members is restrained in a substantially flat shape by the outer circumferential face, and as a result the continuous body surely comes in surface contact with the sheet and is joined.

A manufacturing method of a composite sheet of an absorbent article, wherein preferably the spindle portion side roller is supported on the oscillating arm so that an orientation of the roller in respect to the oscillating arm cannot be changed, in a state in which the outer circumferential face of the spindle portion side roller is facing toward the oscillating end of the oscillating arm.

With this manufacturing method of the composite sheet of an absorbent article, the outer circumferential face of the spindle portion side roller faces toward the oscillating end side roller according to the oscillating movement of the oscillating end side roller. Therefore, even if the oscillating end side roller changes its position in the intersecting direction due to the oscillating movement, the continuous body of the elastic member can be surely fed toward the oscillating end side roller. As a result, stability in the travel state of the continuous body of the elastic member, such as effectively preventing falling off of the continuous body of the elastic member from the oscillating end side roller, is obtained.

Further, the outer circumferential face of the spindle portion side roller can be made to always face the oscillating end, so as to completely synchronize with the oscillating movement of the oscillating arm.

A manufacturing method of a composite sheet of an absorbent article, wherein preferably the intersecting direction is perpendicular to the transporting direction, the rotational central axis direction of the spindle portion is perpendicular to a rotational axis at which the transporting roll is to be rotated in a direction along the transporting direction, the oscillating end side roller is arranged so that a rotational axis of the oscillating end side roller is perpendicular to the rotational central axis direction of the spindle portion, and the spindle portion side roller is arranged so that a rotational axis of the spindle portion is perpendicular to the rotational central axis direction of the spindle portion.

With this manufacturing method of the composite sheet of an absorbent article, orientation of each rotational axis of the transporting roll, the oscillating end side roller, and the spindle portion side roller, is in a perpendicular relationship in respect to the rotational central axis direction of the spindle portion. Therefore, the torsion in the continuous body of the elastic member at the time the continuous body of the elastic member is handed over from the oscillating end side roller to the transporting roll can be suppressed, and the continuous body of the elastic member can be made to surely come in surface contact with the continuous body of the sheet.

A manufacturing equipment of a composite sheet of an absorbent article, the equipment including joining a continuous body of an elastic member in a predetermined meander pattern in respect to a continuous body of a sheet transported continuously in a transporting direction, the equipment including:

a transporting roll that rotates in a direction along the transporting direction and transports the continuous body of the sheet by wrapping around the continuous body of the sheet on an outer circumferential face; and an oscillating arm
that oscillates in an intersecting direction intersecting the transporting direction with a spindle portion as a swivel fulcrum and
that joins the continuous body of the elastic member to a portion of the continuous body of the sheet wrapped around the transporting roll by feeding the continuous body of the elastic member to the continuous body of the sheet, wherein the oscillating arm includes an oscillating end side roller arranged at an oscillating end side of the oscillating arm and a spindle portion side roller arranged at a spindle portion side, wherein the continuous body of the elastic member supplied toward the spindle portion side roller through a supply route along a rotational central axis direction of the spindle portion is put around an outer circumferential face of the spindle portion side roller and an outer circumferential face of the oscillating end side roller successively and guided to the continuous body of the sheet, and wherein a driving force to make the oscillating arm oscillate is input at a position on the oscillating arm different from the spindle portion.

With this manufacturing method of the composite sheet of an absorbent article, the oscillating arm can be oscillated without directly connecting concentrically the drive rotational axis of the driving source of the oscillating arm in respect to the spindle portion. Therefore, the driving source does not have to be arranged close to the spindle portion, and as a result the continuous body of the elastic member can be easily supplied toward the spindle portion through the supply route along the rotational central axis direction of the spindle portion.

Furthermore, the portion at the spindle portion side of the oscillating arm is provided with a spindle portion side roller, and the continuous body of the elastic member is fed to the spindle portion side roller along the rotational central axis direction of the spindle portion. Therefore, movement of the continuous body of the elastic member in the intersecting direction that may occur due to the oscillating movement of the oscillating arm appears mainly as torsion in the portion of the continuous body of the elastic member positioned to the upstream side than the spindle portion side roller and is absorbed there. As a result, falling off of the continuous body of the elastic member from the spindle portion side roller can be effectively prevented. As a result, stability in the travel state of the continuous body of the elastic member is obtained.

The Present Embodiment

A manufacturing method and a manufacturing equipment of a sheet of the present embodiment is applied to, for example, a manufacturing line of a disposable diaper 1 (corresponds to an absorbent article).

Diaper 1

Figure 3A:
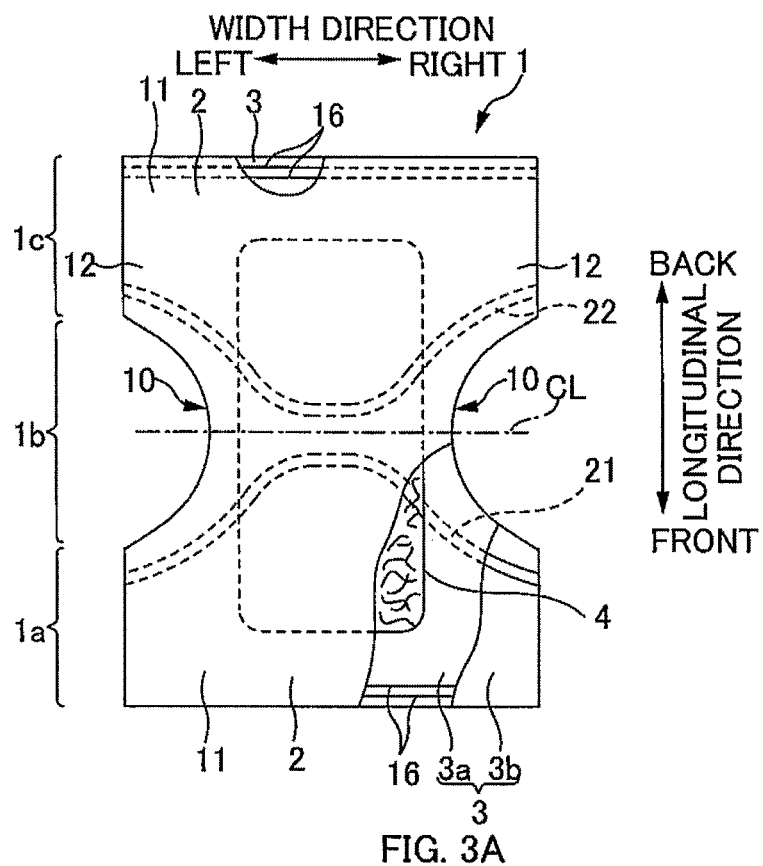
FIG. 3A is a partially cutaway plan view of a diaper 1.
Figure 3B:
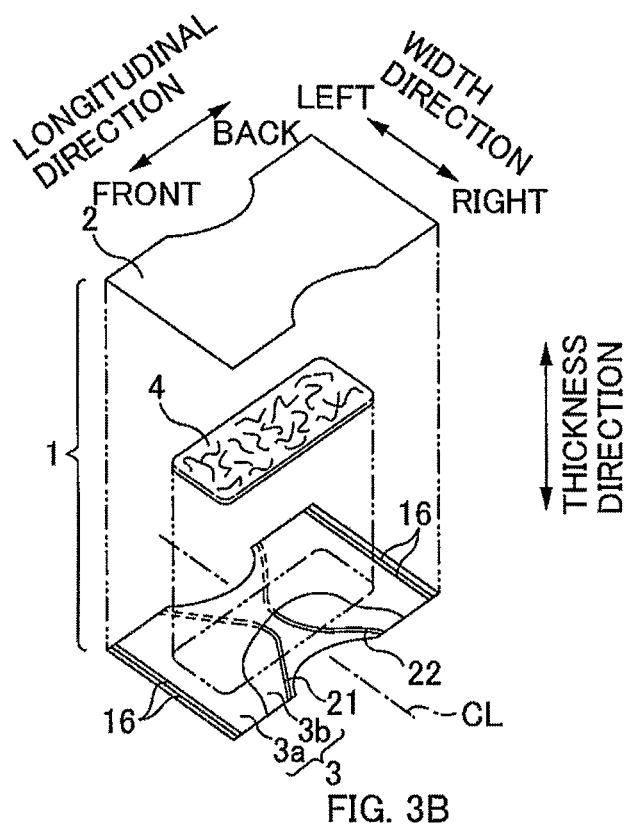
FIG. 3B is an exploded perspective view of the diaper.

FIG. 3A is a partially cutaway plan view of a diaper 1, and FIG. 3B is an exploded perspective view of the diaper. Both diagrams show an expanded state in which a front torso area 1a and a back torso area 1c in a flank portion of a pants-type diaper 1 are separated.

This diaper 1 has a longitudinal direction and a width direction and a thickness direction, that are perpendicular to each other, and along the longitudinal direction of the diaper 1 are defined the front torso area 1a, a crotch area 1b, and the back torso area 1c. Further, the diaper 1 has in the thickness direction, a fluid permeable surface sheet 2, a fluid impermeable back face sheet 3, and a fluid-absorbent absorbent body 4 arranged in between the sheets 2, 3. The surface sheet 2 and the back face sheet 3 are overlapped in a portion extending outward from a peripheral edge of the absorbent body 4, and joined to each other by such as a hot-melt adhesive. Thereby, end edge portion flaps 11 are formed to the front and back in the longitudinal direction and side edge portion flaps 12 are formed to the left and right in the width direction. Note that, in the crotch area 1b of the side edge portion flaps 12, are formed around-leg concave portions 10 that are formed curved inwardly in the width direction, and the diaper 1 is a substantially hourglass shape overall.

For the surface sheet 2, for example, a fluid permeable plastic film or a nonwoven fabric is used.

The back face sheet 3 has an inner sheet 3a facing the surface sheet 2, an outer sheet 3b facing the inner sheet 3a, and both these sheets 3a, 3b are in a same shape and same size to each other, and are joined by adhesion or welding. As the inner sheet 3a, a liquid impermeable plastic film or a nonwoven fabric is used, and as the outer sheet 3b, an air-permeable nonwoven fabric is used.

Each of the end edge portion flaps 11 of the front and back torso areas 1a, 1c are joined with a torso elastic member 16 in a stretched state to the surface and back face sheets 2, 3.

Further, the crotch area 1b and its proximity is provided with a front elastic strip member 21 and a back elastic strip member 22 across and along a width direction of the diaper 1. As these elastic strip members 21, 22, for example, nonwoven fabric having stretchability or strip shaped rubber and the like is used. These elastic strip members 21, 22 each extend in a width direction in a predetermined meander pattern that is curved in a convex shape toward a center line CL that divides the diaper 1 substantially in half to the front and back in the longitudinal direction, and the elastic strip members 21, 22 are provided in between the inner sheet 3a and the outer sheet 3b that structure the back face sheet 3 and, for example, are joined to an inner face of the outer sheet 3b in a stretched state. These front and back elastic strip members 21, 22 cooperate to give elasticity around the around-leg concave portions 10.

Note that, here, a sine curve is illustrated as an example as the meander pattern of these elastic strip members 21, 22, but the meander pattern can be appropriately changed so that the around-leg convex portions 10 can effectively fit around the leg of the wearer of the diaper.

Figure 4:
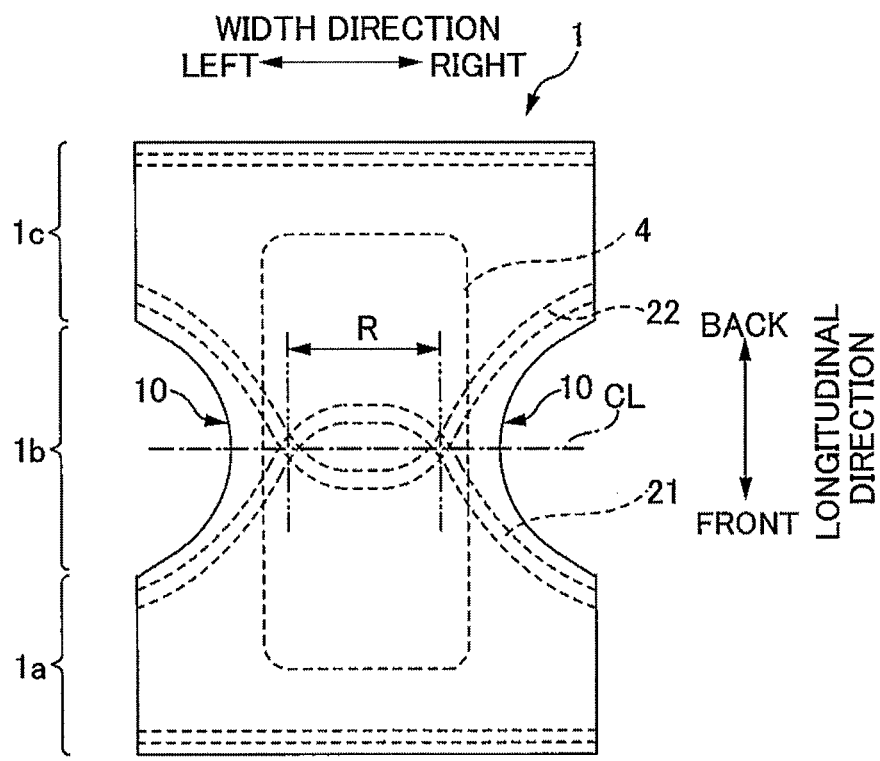
FIG. 4 is a perspective view of the diaper 1 with elastic strip members 21, 22 arranged so as to intersect with each other at a returning portion of each meander pattern.

Further, in order to increase fitting around substantially the entire length of the around-leg concave portion 10, as shown in FIG. 4, the elastic strip members 21, 22 may be arranged to intersect each other at the returning portion of each meander pattern, and further in order to weaken the elasticity in the intersecting region R, a portion of the elastic strip members 21, 22 belonging to the intersecting region R can be divided. Incidentally, elasticity of this intersected region R is weakened because if there is elasticity at the absorbent body 4 portion, creases are formed in the absorbent body 4, and there is fear that fluid absorption performance may deteriorate.

Manufacturing Method and Manufacturing Equipment 30 of a Composite Sheet of this Embodiment Such a diaper 1 is to be completed by a base material of the diaper 1 that is continuously flowing in the manufacturing line being joined and the like with various structural components. The manufacturing method and the manufacturing equipment 30 of the composite sheet according to this embodiment carry out one of the processes. That is, here the manufacturing method and the manufacturing equipment 30 are applied in a process of attaching in the above-described meander pattern a continuous body of an elastic strip member 121 to be the above-described front elastic strip member 21 (corresponds to a continuous body of an elastic member, herein referred to as an elastic strip member 121) and a continuous body of an elastic strip member 122 to be the above-described back elastic strip member 22 (corresponds to a continuous body of an elastic member, herein referred to as an elastic strip member 122) to a continuous body of a sheet 103b to be an outer sheet 3b of the above-described back face sheet 3 (herein referred to as a sheet 103b).

Figure 5:
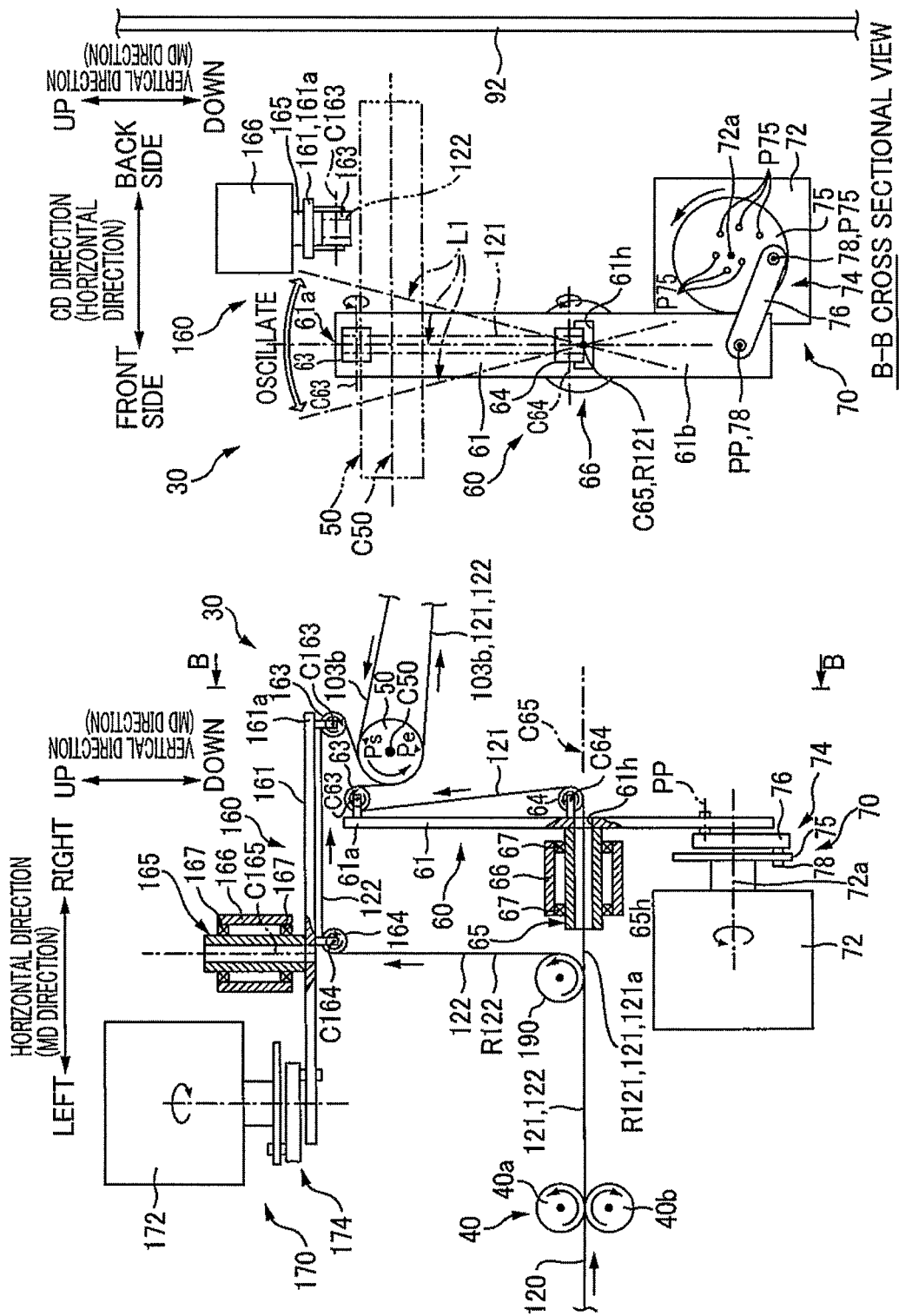
FIG. 5A is a perspective view showing a partially cutaway manufacturing equipment 30 of this embodiment.
FIG. 5B is a cross-sectional view taken along B-B in FIG. 5A.

FIG. 5A is a perspective view showing a partially cutaway manufacturing equipment 30 of this process, and FIG. 5B is a cross-sectional view taken along B-B in FIG. 5A. Note that, hereinbelow, a width direction of the manufacturing equipment 30 is referred to as a CD direction or front side-back side. Further, a direction that is perpendicular to the CD direction is referred to as an MD direction. That is, the MD direction is an arbitrary direction in a plane that is perpendicular to the CD direction. Further, regarding the MD direction, as shown in FIG. 5A, the two direction that are perpendicular to each other are defined as an up-down direction (vertical direction) and a left-right direction (horizontal direction). Incidentally, as shown in FIG. 5B, the CD direction is also in a horizontal direction, and is in a perpendicular relation to the left-right direction in the horizontal direction.

This manufacturing equipment 30 includes (1) a transporting roll 50 that transports the sheet 103b in the MD direction (corresponds to the transporting direction) by wrapping the sheet 103b around in a predetermined wrapping angle and rotating, (2) a slitting apparatus 40 arranged to a left side of the transporting roll 50 and that divides in two in the center in the CD direction a sheet member 120, that is an original sheet made of an elastic strip member that is sent continuously from the left, and forms a pair of elastic strip members 121, 122, (3) a first guide member 60 that continuously feeds the elastic strip member 121 in a stretched state to a portion of the sheet 103b that is wrapped around an outer circumferential face of the transporting roll 50 and joins them, and (4) a second guide member 160 that continuously feeds the elastic strip member 122 in a stretched state to a portion of the same sheet 103b and joins them.

These first and second guide members 60, 160 each feed the elastic strip members 121, 122 that they are in charge of toward the sheet 103b in the MD direction and reciprocates the elastic strip members 121, 122 in the CD direction (corresponds to an intersecting direction). Thus, each of the elastic strip members 121, 122 are overlapped on the sheet face of the sheet 103b and joined while the joining position to the sheet 103b in the CD direction is changed every moment continuously. As a result, the sheet face of the sheet 103b is attached in a surface contact state with a pair of the elastic strip members 121, 122 in an intended meander pattern such as a sine curve.

Incidentally, it is needless to say that before joining each of the elastic strip members 121, 122 to the sheet 103b, a hotmelt adhesive is to be applied to each of the elastic strip members 121, 122 by an adhesive applying apparatus that is not shown.

Hereinbelow, each structural element 40, 50, 60, 160 is described. Note that, in the below description, unless specifically stated, each structural device according to the manufacturing equipment 30 is cantilevered via an appropriate bracket that is not shown by a vertical support wall 92 (namely a panel) that extends along an entire length of the manufacturing equipment 30 in the MD direction. That is, as shown in FIG. 5B, at a back side in the CD direction (a back side of a plane of paper in FIG. 5A) is provided the support wall 92 along a direction substantially parallel to the MD direction (a direction substantially parallel to the plane of paper). A vertical wall face of this support wall 92 supports portions at the back side in the CD direction of each structural device, and portions at the front side are in a not supported state.

(1) Transporting Roll 50

The transporting roll 50 has a cylindrical body with a rotational axis C50 in the horizontal CD direction as a main body, and rotates anti-clockwise in a predetermined peripheral speed in a direction along the MD direction as a rotational direction. This transporting roll 50 is supplied with the sheet 103b from the right substantially horizontally, for example. With an approximately 12 o'clock position at an upper portion of the transporting roll 50 as a wrap around starting position Ps, the sheet 103b is wrapped around an outer circumferential face of the transporting roll 50, from the position Ps at a wrap around angle of, for example, 180° to 200°, and its transporting direction is reversed. Ultimately, the sheet 103b is fed to the right in the substantially horizontal direction, with an approximately 6 o'clock position at a lower portion of the transporting roll 50 as a wrap around finishing position Pe (corresponds to transporting).

This transporting roll 50 may be structured as a drive roll that rotatingly drives with an appropriate motor and the like as a driving source, or may be structured as a follower roll that is rotatingly driven by the sheet 103b.

(2) Slitting Apparatus 40

A slitting apparatus 40 has a top and bottom pair of discal rotating blades 40a, 40b in the center in the CD direction. When passing these rotating blades 40a, 40b, the sheet member 120 that is an original plate of the elastic strip members 121, 122 is divided in half, and thereby a pair of the elastic strip members 121, 122 is produced. The elastic strip members 121, 122 are each fed to a first guide member 60 and a second guide member 160.

(3) First Guide Member 60

The first guide member 60 has a tabular oscillating arm 61 provided to the left of the transporting roll 50. The oscillating arm 61 is arranged so as to cross over the rotational axis C50 of the transporting roll 50 up and down in the vertical direction. Then, with a spindle portion 65 positioned lower than the rotational axis C50 as a swivel fulcrum, the oscillating end 61a positioned above the rotational axis C50 can be made to oscillate in the CD direction.

Further, the drive mechanism 70 of the oscillating movement is a motor 72 combined with a crank mechanism 74, and these will be described later. Further, the spindle portion 65 is, for example, a shaft body 65 that protrudes integrally and to the left from a surface on the left side of the oscillating arm 61, and is rotatably supported inside an outer cylindrical member 66 via bearings 67. The outer cylindrical member 66 is fixed to the support wall 92 via an appropriate bracket that is not shown, and thus the oscillating arm 61 is supported to be able to swivel around a rotational central axis C65 of the spindle portion 65.

On a right side surface of the oscillating arm 61 that is a surface on a side opposing the transporting roll 50 are rotatably supported a pair of rollers 63, 64 each around substantially horizontal rotational axes C63, C64. One of the roller 63 is an oscillating end side roller 63 provided on an oscillating end 61a, and the other roller 64 is a spindle portion side roller 64 provided at a position toward the spindle portion 65 side than the oscillating end side roller 63.

Thus, the elastic strip member 121 of the elastic strip members 121, 122 fed from the above-described slitter apparatus 40 is first fed from the left to the right along the horizontal direction, and then the elastic strip member 121 passes a through hole 65h formed passing through within the spindle portion 65 in the horizontal direction (this through hole 65h will be described later) and out a right side surface of the oscillating arm 61. Then, the elastic strip member 121 is put around an outer circumferential face of the spindle portion side roller 64 that has been set on the same surface to be guided to an upper oscillating end 61a. Then, the elastic strip member 121 is wrapped around an outer circumferential face of the oscillating end side roller 63 at the oscillating end 61a, and after its travel direction has been reversed substantially downward by the wrapping around, the elastic strip member 121 is supplied from upper left of the transporting roll 50 to a wrap around range Ps to Pe of the sheet 103b.

Then while supplying the elastic strip member 121, the oscillating end side roller 63 reciprocates in the CD direction due to an oscillating movement of the oscillating end 61a. Thereby the elastic strip member 121 is joined to the sheet face of the sheet 103b in an intended meander pattern by continuously changing the joining position in the sheet surface of the sheet 103b in the CD direction. Further, at the time of supplying the elastic strip member 121, the elastic strip member 121 is restrained to a substantially flat shape by being wrapped around the outer circumferential face of the spindle portion side roller 64 and the outer circumferential face of the oscillating end side roller 63, so that the elastic strip member 121 is joined in respect to the sheet 103b in a surface contacting state (corresponds to joining).

Further, as shown in FIG. 5B, each of the oscillating end side roller 63 and the spindle portion side roller 64 is arranged on a straight line L1 that connects the oscillating end 61a and the rotational central axis C65 of the spindle portion 65. Further, the oscillating end side roller 63 is fixed to the oscillating arm 61 so that its outer circumferential face is facing toward the rotational central axis C65 of the spindle portion 65 and its orientation in respect to the oscillating arm 61 cannot be changed. On the other hand, the spindle portion side roller 64 is also fixed to the oscillating arm 61 so that its outer circumferential face is facing toward the oscillating end 61a of the oscillating arm 61 and its orientation in respect to the oscillating arm 61 cannot be changed.

Thus, with this structure, according to the reciprocating movement of the oscillating end side roller 63, the outer circumferential face of the spindle portion side roller 64 is always facing toward the oscillating end side roller 63, so that the elastic strip member 121 can be surely fed toward the oscillating end side roller 63. As a result, stability of the travel state of the elastic strip member 121 can be obtained, such as the elastic strip member 121 falling off from the oscillating end side roller 63 can be effectively prevented.

Further, according to the above structure, the rotational axis C63 of the oscillating end side roller 63 and the rotational axis C64 of the spindle portion side roller 64 are always maintained in a parallel state, regardless of the oscillating movements of the oscillating arm 61. Thus, a difference in tension that applies on both end edges of the elastic strip member 121 in the width direction that might occur due to the oscillating movements of the oscillating arm 61 can be surely alleviated, and as a result, the elastic strip member 121 falling off from the oscillating end side roller 63 and the spindle portion side roller 64 can be effectively prevented.

Further, in order to obtain stability in the travel state, as shown in FIG. 5A, a supply route R121 of the elastic strip member 121 to the spindle portion side roller 64 is aligned in a straight line to the rotational central axis C65 of the spindle portion 65, and the roller 64 is arranged so that the outer circumferential face of the spindle portion side roller 64 is in contact with the rotational central axis C65 of the spindle portion 65. Thus, movement of the elastic strip member 121 in the CD direction that may occur due to the oscillating movement of the oscillating arm 61, appears mainly as a torsion in the portion 121a of the elastic strip member 121 at an upper side than the spindle portion side roller 64 and is absorbed there, and as a result the elastic strip member 121 falling off from the roller 64 can be effectively prevented.

Further, according to this structure, the spindle portion side roller 64 is arranged so that the outer circumferential face of the spindle portion side roller 64 is in contact with the rotational central axis C65 of the spindle portion 65, so that a travel amount of the roller 64 in the CD direction that may occur with the oscillating movement of the oscillating 61 can be made to approximately zero, and thus the elastic strip member 121 falling off from the roller 64 can be effectively prevented.

Incidentally, in this embodiment, as the drive mechanism 70 of the oscillating arm 61, a so-called direct drive, namely, a structure in which the spindle portion 65 is directly connected with a drive rotational axis 72a of a driving source such as a motor is not used, and the driving force of the driving source is transferred to the oscillating arm 61 via the crank mechanism 74. This is due to the following two reasons.

The first reason is to ensure the above described preferable supply route R121 regarding the supply of the elastic strip member 121. Described in more detail, as shown in FIG. 5A, in relation to the arrangement position of the slit apparatus 40, the elastic strip member 121 is supplied from the left of the oscillating arm 61. However, the spindle portion 65 is positioned to the left of the oscillating arm 61. Therefore, in the case where the drive rotational axis 72a of the motor 72 is matched with the spindle portion 65 and connected directly, this motor 72 gets in the way and it becomes difficult to set the preferable supply route R121 of the elastic strip member 121 as described above, that is a supply route R121 that is aligned in a straight line with the rotational central axis C65 of the spindle portion 65.

On the contrary, in the case where a driving force of the oscillating movement of the oscillating arm 61 is to be input to a position PP different from the spindle portion 65 by the crank mechanism 74, as in this embodiment shown in FIG. 5A, by forming the through hole 65h in respect to the spindle portion 65 substantially concentrically as the rotational central axis C65 of the spindle portion 65, and also passing through the elastic strip member 121 in the through hole 65h, the supply route R121 of the elastic strip member 121 aligned in a straight line with the rotational central axis C65 of the spindle portion 65 described above can be secured. As a result, the travel state of the elastic strip member 121 can be stabilized. Note that, such a through hole 65h can be expressed as a communicating space for communicating a side opposing the transporting roll 50 (right side) and a side not opposing the transporting roll 50 (left side). Further, it is needless to say that the oscillating arm 61 is also formed with a through hole 61h in the left to right direction so as to correspond with the through hole 65h.

The second reason is to increase movement stability in oscillation of the oscillating arm 61. Namely, in the case where the crank mechanism 74 is used, at the time of making the oscillating arm 61 perform the oscillating movement, the drive rotational axis 72a of the motor 72 needs only to be rotated in one direction, that is, the drive rotational axis 72a of the motor 72 does not have to be rotated in the forward and reverse direction. As a result, since at least switching control does not lie in the rotation direction of the motor 72, stability in the oscillating movement of the oscillating arm 61 becomes outstanding.

Such a crank mechanism 74 (corresponds to a conversion transmission mechanism) has on a drive rotating axis 72a of the motor 72 in a horizontal direction in the MD direction a circular disk member 75 (corresponds to a rotating member) that has been fixed integrally and concentrically and a rod-shaped link member 76 (corresponds to a connecting member) that connects the disk member 75 and a power point PP of the oscillating arm 61. Then, a position eccentric from a drive rotating axis 72a in the disk member 75 is connected with an end portion of the link member 76 by a coupling pin 78 or the like. Thus, every time the disk member 75 rotates once, the link member 76 is reciprocated once only in its longitudinal direction, and the oscillating arm 61 performs an oscillating movement only once by this one reciprocating movement.

Note that, here, as connecting positions of the link member 76 in the disk member 75, there may preferably be prepared a plurality of positions P75, P75 . . . , and moreover these plurality of positions P75, P75 . . . may be different from each other in their eccentric amounts that is a distance to the drive rotating axis 72a. If it is set in this way, it is possible to easily change an amplitude amount of the oscillating movement of the oscillating arm 61 by selecting each connecting position P75, P75 . . . on the disk member 75. Thus, if each connecting position P75, P75 . . . is set in advance corresponding to the size of the disposable diaper 1, thereafter the operator needs only to select the connecting position P75 of a size to be manufactured next, to be able to switch easily and immediately to a meander pattern corresponding to the relevant size. Thus, it becomes possible to remarkably shorten a down time that accompanies size changing of the disposable diaper 1.

Further, as in the example in FIG. 5B, preferably each of the connecting positions P75, P75 . . . may be set in positions different from each other in regard to a circumferential direction of the disk member 75. In the illustrated example, a rotation radius that is an eccentric amount of the connecting positions P75, P75 . . . are gradually decreased as it progresses along one direction in the circumferential direction of the disk member 75, as if these connecting positions P75, P75 . . . exist on one whirl line in appearance. In the case where positions in the circumferential direction of each of the connecting positions P75, P75 . . . are different from each other in this way, supposing that in the case where a difference in an eccentric amount of one connecting position P75 and an eccentric amount of another connecting position P75 is small, interference of the connecting positions P75, P75 . . . from each other can be effectively avoided.

For example, in the case where the coupling pin 78 is used to connect the disk member 75 and the link member 76, it is necessary to provide pin holes to the disk member 75 side, and it is possible to avoid these pin holes from becoming connected to each other. Thus, it is possible to change the eccentric amounts of these connecting positions P75 in small increments, and as a result it is possible to change the amplitude amount of the oscillating arm 61 in small increments.

Incidentally, if a curve that connects these connecting positions P75, P75 . . . is in a whirl shape as described above, the operator can instantly recognize a size of amplitude corresponded to each connecting position P75 based on the aligning order of the connecting positions P75 in the circumferential direction of the disk member 75. Therefore, it is possible to decrease frequency in occurrence of selecting mistakes of the connecting position P75 at the time of changing the size.

Figure 6:
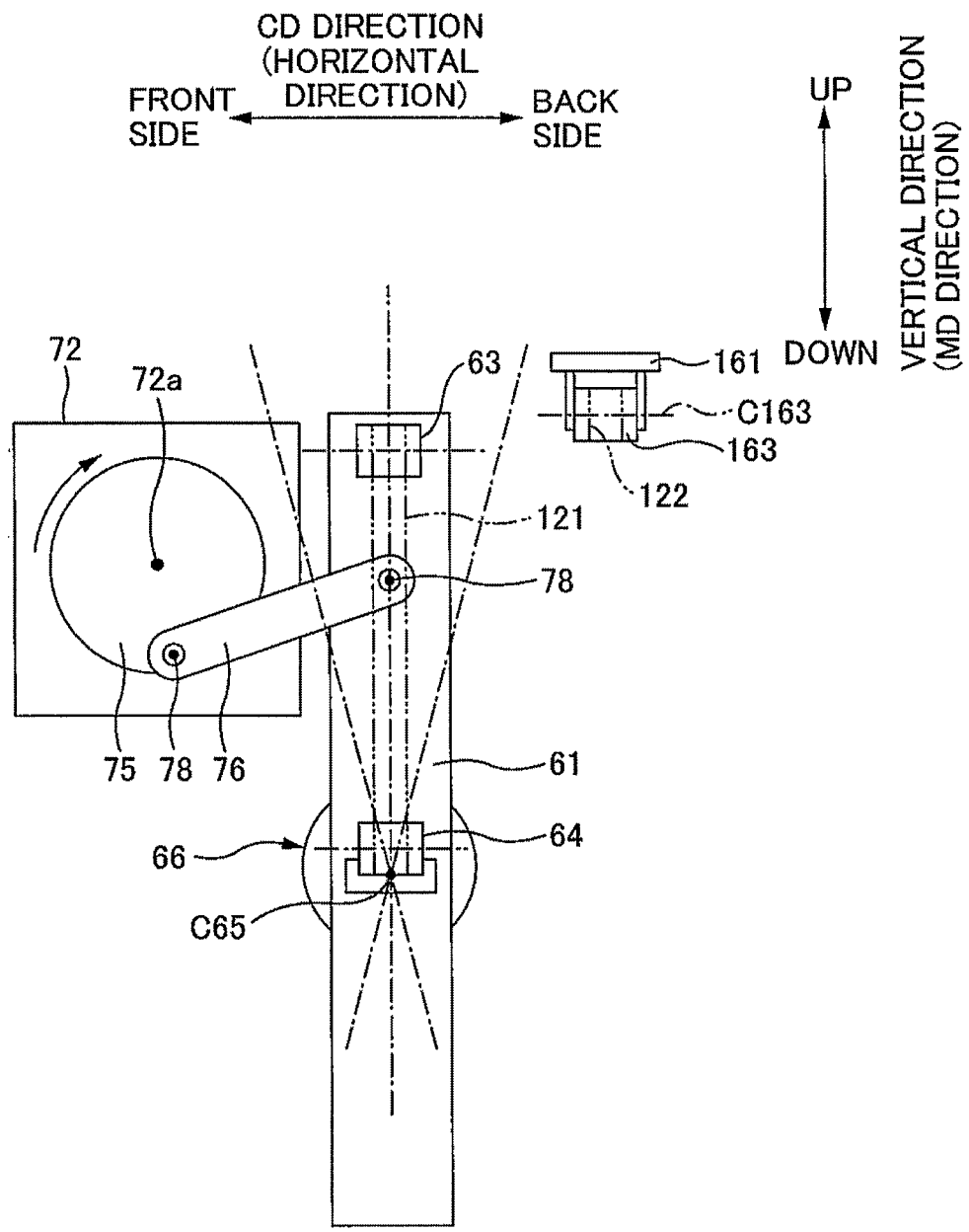
FIG. 6 is an explanatory diagram showing other examples of positions of points PP where a force is applied on an oscillating arm.

By the way, as shown in FIG. 5B, the power point PP of the oscillating arm 61 of this embodiment is provided at a position that is at an opposite side to the oscillating end 61a of the oscillating arm 61 sandwiching a rotational central axis C65 of the spindle portion 65. That is, the oscillating arm 61 has an extending portion 61b that extends toward an opposite side of the oscillating end 61a from the spindle portion 65, and a power point PP is set at an end portion of the extending portion 61b. An end portion of the link member 76 is connected to this power point PP by a coupling pin 78 and the like. However, the position of the power point PP is not limited to the above as long as it is at a portion other than the spindle portion 65. For example, as shown in FIG. 6, the PP may be set at a portion in between the spindle portion 65 and the oscillating end 61a of the oscillating arm 61. Note that, selection of either the structure in FIG. 5B or the structure in FIG. 6 is decided based on the layout of the motor 72 and the crank mechanism 74 and the like.

(4) The Second Guide Member 160

The second guide member 160 is a member with roughly the same structure as the above-described first guide member 60. As shown in FIG. 5B, the second guide member 160 is arranged more to the back side than the first guide member 60 in the CD direction. Thus, the elastic strip member 122, that this second guide member 160 is in charge of, is attached more to the back side in the CD direction than the elastic strip member 121 and in parallel thereto, the elastic strip member 121 being attached to the sheet 103b by the first guide member 60. However, according to the disposable diaper 1, as shown in FIG. 4, an arrangement pattern in which the elastic strip member 121 and the elastic strip member 122 are partially overlapped is possible. In that case, if the first guide member 60 and the second guide member 160 are arranged in parallel, these guide members 60, 160 will come in collision with each other and cannot form the above-described pattern.

Here, in order to avoid the above collision, as shown in FIG. 5A, the position of the second guide member 160 in a circumferential direction Dc of the transporting roll 50 is made different from that of the first guide member 60. That is, the second guide member 161 is arranged displaced to an upstream side in the circumferential direction Dc than the first guide member 61.

In more detail, as shown in FIG. 5A, the oscillating arm 161 of the second guide member 160 is at a position in which the oscillating arm 61 of the first guide member 60 is rotatingly moved to an upstream side in the circumferential direction Dc for a predetermined rotating angle θ only around an imaginary axis, that is not shown, parallel to the rotational axis C50 of the transporting roll 50, the rotating angle θ being 90° in the shown example. Thus, the oscillating arm 161 is arranged above the first guide member 60 and the transporting roll 50, and striding over the rotational axis C50 of the transporting roll 50 to the left and right in the horizontal direction. With the spindle portion 165 that is positioned more to the left of the rotational axis C50 as a swivel fulcrum, the oscillating end 161a positioned more to the right than the rotational axis C50 is structured so as to be able to oscillate in the CD direction.

The driving mechanism 170 for the oscillating movement is the motor 172 combined with the crank mechanism 174, as in the case for the first guide member 160. Further, the spindle 165 is a shaft body 165 that extends integrally and upwards from an upper surface of the oscillating arm 161, as similar to the case with the first guide member 160, and this shaft body 165 is supported rotatably in an outer cylindrical member 166 via the bearings 167. Note that, the outer cylindrical member 166 is fixed to the support wall 92.

Further, on a lower surface of the oscillating arm 161 which is a surface on a side opposing the transporting roll 50, each of a pair of rollers 163, 164 is rotatably supported around horizontal rotating axes C163, C164. One roller 163 is an oscillating end side roller 163 provided at an oscillating end 161a, and another roller 164 is a spindle portion side roller 164 provided more to the spindle portion 165 than the oscillating end side roller 163.

Therefore, the elastic strip member 122 that is fed from the slitter apparatus 40 is fed from the left to the right in the horizontal direction, while being in parallel in the CD direction next to the elastic strip member 121 that is sent to the above-described first guide member 60. At a position in which a rotational central axis C165 of the spindle portion 165 of the second guide member 160 matches a plan position, a travel direction of the elastic strip member 122 is changed upwards in the vertical direction by a direction changing roller 190 to reach the spindle portion side roller 164, and is put around the outer circumferential face of the spindle portion side roller 164. Then, with the spindle portion side roller 164, the elastic strip member 122 is guided to the oscillating end 161a that is to the right than the transporting roll 50, and thereafter, after the travel direction is reversed to the left by the oscillating end side roller 163 at the oscillating end 161a, the elastic strip member 122 is supplied close to the wrap around starting position of the sheet 103b from the upper right of the transporting roll 50.

Then, during the above supplying, the oscillating end side roller 163 reciprocates in the CD direction due to the oscillating movement of the oscillating end 161a, thus the elastic strip member 122 is joined to a sheet face of the sheet 103b in a desired meander pattern with its joining position in the sheet face of the sheet 103b being continuously changed in the CD direction. Further, at the time of this supply, the elastic strip member 122 is restrained in a substantially flat shape by wrapping around the outer circumferential face of the spindle portion side roller 164 and an outer circumferential face of the oscillating end side roller 163, so that the elastic strip member 122 is joined to the sheet 103b in a surface contact state.

Note that, the structure shown in below (a) to (c) are all the same as those for the first guide member 60, and therefore their detailed description is omitted.

(a) Each of the oscillating end side roller 163 and the spindle portion side roller 164 are arranged on a straight line that connects the oscillating end 161a of the oscillating arm 161 and the rotational central axis C165 of the spindle portion 165.

(b) The oscillating end side roller 163 is fixed to the oscillating arm 161 so that its outer circumferential face is facing toward the rotational central axis C165 of the spindle portion 165 of the oscillating arm 161 with its orientation in respect to the oscillating arm 161 being unable to be changed and the spindle portion side roller 164 is also fixed to the oscillating arm 161 so that its outer circumferential face is facing toward the oscillating end 161a of the oscillating arm 161 with its orientation in respect to the oscillating arm 161 being unable to be changed.

(c) The supply route R122 of the elastic strip member 122 to the spindle portion side roller 164 is aligned in one line with the rotational central axis C165 of the spindle portion 165, and the spindle portion side roller 164 is arranged so that the circumferential face of the spindle portion side roller 164 is contacting the rotational central axis C165 of the spindle portion 165.

Other Embodiments

The embodiments of the present invention have been described above, but the present invention is not limited to the embodiments, and below modifications are possible.

In the above-described embodiment, the crank mechanism 74 (174) is illustrated as a conversion transmission mechanism that transfers the rotating movement of the drive rotating axis 72a of the motor 72 by converting it to a reciprocating movement to the oscillating arm 61 (161), and the power point PP is set to an end portion of the extending portion 61b of the oscillating arm 61. As long as a power point PP is set at a position different from the spindle portion 65 (165) however, it is not limited thereto.

Figure 7:
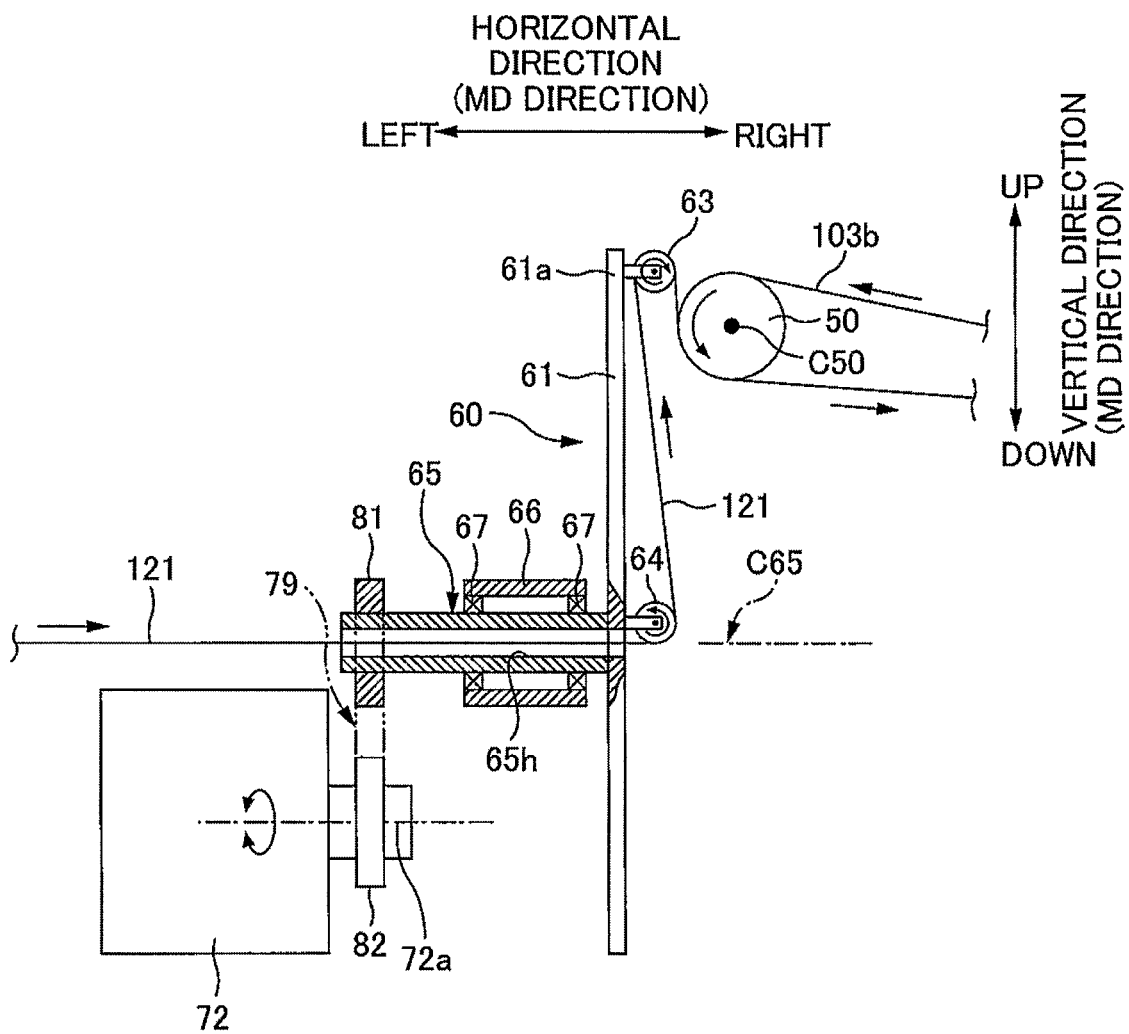
FIG. 7 is an explanatory diagram showing another embodiment of a driving mechanism 70 (170).

For example, as shown in FIG. 7, the drive rotational axis 72a of the motor 72 may be arranged in parallel in respect to the spindle portion 65, with pulleys 81, 82 provided fixed to both the spindle portion 65 and the drive rotational axis 72a, and an endless belt 79 may be put around these pulleys 81, 82, and a driving force that is needed for the oscillating movement of the oscillating arm 61 may be transferred from the drive rotational axis 72a to the spindle portion 65 via the endless belt 79. Note that, in this case, it is needless to say that the drive rotational axis 72a is to be controlled to repeat a forward and reverse rotation.

Further, as a driving source to drive the oscillating arm 61 (161), a cylinder in which a piston appears by an appropriate working fluid such as a hydraulic fluid or air may be used. In this case, for example, on the one hand the piston is to be connected to the oscillating arm 61 (161), whereas the cylinder is to be attached to the support wall 92 via an attaching mechanism that can oscillate such as a trunion or a crevice shape.

In the above-described embodiment, the manufacturing method of a composite sheet according to this invention is applied for manufacturing of the pants type diaper 1, but it is not limited thereto and may be applied for manufacturing of expanding type diapers (a type of diaper in which the front torso area 1a and the back torso area 1c are held fixed by a tape fastener when wearing).

In the above-described embodiment, there is illustrated a structure in which an oscillating arm 61 (161) has two rollers of an oscillating end side roller 63 (163) and a spindle portion side roller 64 (164), but it is not limited thereto, and one roller may be provided in between the oscillating end side roller 63 (163) and the spindle portion side roller 64 (164). Note that, in this case the rotating axis of the roller to be additionally provided may be in parallel to the rotational axis C64 (C164) of the spindle portion side roller 64 (164).

In the above-described embodiment, as shown in FIG. 5A, the rotational central axis C65 of the spindle portion 65 of the first guide member 60 is oriented in the left-right direction (horizontal direction), the rotational central axis C165 of the spindle portion 165 of the second guide member 160 is oriented in the up-down direction (vertical direction), and the rotational axis C50 of the transporting roll 50 is oriented in the CD direction (horizontal direction). However, it is not limited thereto, as long as the rotational central axis C65 (C165) of the spindle portion 65 (165) of the first guide portion 60 or the second guide portion 160 and the rotational axis C50 of the transporting roll 50 are in a perpendicular relationship with each other.

In the above-described embodiment, the rotational axis C63 (C163) of the oscillating end side roller 63 (163) and the rotational axis C64 (C164) of the spindle portion side roller 64 (164) are in the substantially horizontal direction. The reason is to hand over the elastic strip member 121 (122) in a substantially flat shape with little torsion in respect to the transporting roll 50 with the rotational axis C50 in the horizontal direction that is the CD direction. Thus, the orientation of the rotational axes C63 (C163), C64 (C164) of the oscillating end side roller 63 (163) and the spindle portion side roller 64 (164) is not limited to a substantially horizontal direction in any way, and can be changed according to a direction in which the rotational axis C50 of the transporting roll 50 faces. That is, the rotational axis C63 (C163) of the oscillating end side roller 63 (163) and the rotational axis C64 (C164) of the spindle portion side roller 64 (164) may be arranged so that the face that the rotational axes C63 (C163), C64 (C164) make with the oscillating movement of the oscillating arm 61 (161) is to be parallel to the rotational axis C50 of the transporting roll 50. Furthermore, the oscillating end side roller 63 (163) and the spindle portion side roller 64 (164) may be arranged so that the rotational axes C63 (C163), C64 (C164) become perpendicular to the rotational central axis C65 (C165) of the spindle portion 65 (165) that is in a perpendicular relationship with the rotational axis C50 of the transporting roll 50.

In the above-described embodiment, a flat bone roll that has a circumferential face that is flat across the width direction (CD direction) of the roller is used as the oscillating end side roller 63 (163) and the spindle portion side roller 64 (164), but it is not limited thereto in any way. For example, a crowned roller may be used. This crowned roller refers to a roller with a largest diameter portion of the roller set in a central portion in the width direction. With this roller, the elastic strip member 121 (122) put around the outer circumferential face is given a centripetal force toward the central portion in the width direction of the roller by the largest diameter portion of the outer circumferential face so that it becomes difficult for the elastic strip member 121 (122) to fall off from the roller. As an example such a crowned roller, there may be, for example, such as a roller formed with annular ribs along a circumferential direction in only the central portion in the outer circumferential face, or a roller that has a radius that gradually increases from end portions toward the central portion of the outer circumferential face.

In the above-described embodiment, a hot-melt adhesive was applied with an adhesive applying apparatus to the elastic strip members 121, 122, but it is not limited thereto in any way as long as the sheet 103b and the elastic strip members 121, 122 can be joined together. For example, the adhesive may be applied to just the sheet 103b, or to both the elastic strip members 121, 122 and the sheet 103b.

REFERENCE SIGNS LIST 1 disposable diaper (absorbent article), 1a front torso area, 1b crotch area, 1c back torso area, 2 surface sheet, 3 back face sheet, 3a inner sheet, 3b outer sheet, 4 absorbent body, 10 around-leg concave portions, 11 end edge portion flaps, 12 side edge portion flaps, 16 torso elastic member, 21 front elastic strip member, 22 back elastic strip member, 30 manufacturing equipment, 40 slitting apparatus, 40a discal rotating blade, 40b discal rotating blade, 50 transporting roll, 60 first guide member, 61 oscillating arm, 61a oscillating end, 61b extending portion, 61h through hole, 63 oscillating end side roller, 64 spindle portion side roller, 65 spindle portion, 65h through hole, 66 outer cylindrical member, 67 bearings, 70 drive mechanism, 72 motor (driving source), 72a drive rotational axis, 74 crank mechanism (conversion transmission mechanism), 75 circular disk member (rotating member), 76 rod-shaped link member (connecting member), 78 coupling pin, 79 endless belt, 81 pulley, 82 pulley, 92 support wall, 103b sheet (continuous body of a sheet), 120 sheet member, 121 elastic strip member (continuous body of elastic member), 121a portion, 122 elastic strip member (continuous body of an elastic member), 160 second guide member, 161 oscillating arm, 161a oscillating end, 163 oscillating end side roller, 164 spindle portion side roller, 165 spindle portion, 166 outer cylindrical member, 167 bearings, 170 driving mechanism, 172 motor (driving source), 174 crank mechanism (conversion transmission mechanism), 190 direction changing roller, CL center line, C50 rotational axis, C63 rotational axis, C64 rotational axis, C65 rotational central axis, C163 rotational axis, C164 rotational axis, 0165 rotational central axis, R121 supply route, R122 supply route, R region, P75 connecting position, PP power point, Pe finishing position, Ps starting position

The invention claimed is:

1. A method of manufacturing a composite sheet of an absorbent article, the method including joining a continuous body of an elastic member in a predetermined meander pattern in respect to a continuous body of a sheet transported continuously in a transporting direction, the method comprising:
   transporting the continuous body of the sheet by wrapping the continuous body of the sheet around an outer circumferential face of a transporting roll that rotates in a direction along the transporting direction; and
   joining the continuous body of the elastic member to a portion of the continuous body of the sheet wrapped around the transporting roll by feeding the continuous body of the elastic member to the continuous body of the sheet via an oscillating arm that oscillates by a driving force in an intersecting direction intersecting the transporting direction with a spindle portion as a swivel fulcrum,
   wherein the oscillating arm includes an oscillating end side roller arranged at an oscillating end side of the oscillating arm and a spindle portion side roller arranged at a spindle portion side,
   wherein in the joining, the continuous body of the elastic member supplied toward the spindle portion side roller through a supply route along a rotational central axis of the spindle portion is put around an outer circumferential face of the spindle portion side roller and an outer circumferential face of the oscillating end side roller successively and guided to the continuous body of the sheet, wherein the driving force is applied to the oscillating arm at a position different from a position of the spindle portion, and wherein the rotational central axis of the spindle portion is tangential with an outer circumferential face of the spindle portion side roller.

2. A The method according to claim 1, wherein
the oscillating end side roller and the spindle portion side roller are arranged on a face of the oscillating arm on a side opposing the transporting roll, the spindle portion has a communicating space that communicates the side opposing the transporting roll and a side not opposing the transporting roll, along the rotational central axis of the spindle portion, the continuous body of the elastic member that is fed through the supply route along the rotational central axis of the spindle portion reaches a face of the oscillating arm on the side not opposing the transporting roll, and ends at the spindle portion side roller by passing through the communicating space.

3. The method according to claim 2, wherein the communicating space is a through hole in the spindle portion along the rotational central axis of the spindle portion.

4. The method according to claim 1, wherein
when the driving force is applied to the oscillating arm,
rotatingly a driving source about a drive rotational axis thereof and converting, by a conversion transmission mechanism, a rotating movement of the drive source to a reciprocating movement and transmitting, by the conversion transmission mechanism, the reciprocating movement to the oscillating arm, the conversion transmission mechanism has
a rotating member rotating about the drive rotational axis and a coupling member that couples the oscillating arm at the position where the driving force is applied to the oscillating arm to the rotating member a position eccentric from the drive rotational axis of the rotating member, and the rotating member is set with a plurality of the eccentric positions each having different eccentric amounts from each other.

5. The method according to claim 1, wherein
the transporting roll rotates around a rotational axis,
the oscillating end side roller and the spindle portion of the oscillating arm are arranged so as to sandwich the rotational axis of the transporting roll in between, and a direction of travel of the continuous body of the elastic member is reversed by the oscillating end side roller and the continuous body of the elastic member is supplied to the transporting roll.

6. The method according to claim 1, wherein
the spindle portion side roller is fixed to the oscillating arm in a state in which the outer circumferential face of the spindle portion side roller is facing toward the oscillating end of the oscillating arm.

7. The method according to claim 1, wherein
the intersecting direction is perpendicular to the transporting direction, the rotational central axis of the spindle portion is perpendicular to a rotational axis about which the transporting roll is to be rotated, the oscillating end side roller is arranged so that a rotational axis of the oscillating end side roller is perpendicular to the rotational central axis of the spindle portion, and the spindle portion side roller is arranged so that a rotational axis of the spindle portion side roller is perpendicular to the rotational central axis of the spindle portion.

* * * * *